US006210710B1

(12) United States Patent
Skinner

(10) Patent No.: US 6,210,710 B1
(45) Date of Patent: Apr. 3, 2001

(54) SUSTAINED RELEASE POLYMER BLEND FOR PHARMACEUTICAL APPLICATIONS

(75) Inventor: George William Skinner, Wilmington, DE (US)

(73) Assignee: Hercules Incorporated, Wilmington, DE (US)

(*) Notice: Subject to any disclaimer, the term of this patent is extended or adjusted under 35 U.S.C. 154(b) by 0 days.

(21) Appl. No.: 08/847,842

(22) Filed: Apr. 28, 1997

(51) Int. Cl.[7] .............. A61K 9/20; A61K 9/22; A61K 9/28

(52) U.S. Cl. .......... 424/464; 424/435; 424/451; 424/455; 424/456; 424/470; 424/468; 514/770; 514/772.3; 514/777; 514/778; 514/779; 514/780; 514/781; 514/782; 514/784

(58) Field of Search .................. 424/464, 468, 424/469, 474, 470, 484, 485, 486, 487, 488, 435, 451, 455, 456, 465

(56) References Cited

U.S. PATENT DOCUMENTS

| | | | |
|---|---|---|---|
| 3,065,143 | 11/1962 | Christenson et al. | 167/82 |
| 3,362,880 | 1/1968 | Jeffries | 167/82 |
| 3,362,881 | 1/1968 | Eberhardt et al. | 167/82 |
| 3,555,151 | 1/1971 | Kaplan et al. | 424/156 |
| 3,870,790 | 3/1975 | Lowey et al. | 424/19 |
| 4,140,755 | 2/1979 | Sheth et al. | 424/21 |
| 4,167,558 | 9/1979 | Sheth et al. | 424/22 |
| 4,226,849 | 10/1980 | Schor | 424/19 |
| 4,259,314 | 3/1981 | Lowey | 424/19 |
| 4,357,469 | 11/1982 | Schor | 536/91 |
| 4,369,172 | 1/1983 | Schor | 424/19 |
| 4,389,393 | 6/1983 | Sheth et al. | 424/22 |
| 4,424,235 * | 1/1984 | Sheth et al. | 424/319 |
| 4,540,566 | 9/1985 | Davis et al. | 424/22 |
| 4,680,323 | 7/1987 | Lowey | 524/43 |
| 4,699,779 * | 10/1987 | Palinczar | 424/59 |
| 4,704,285 | 11/1987 | Alderman | 424/468 |
| 4,756,911 | 7/1988 | Drost et al. | 424/468 |
| 4,871,548 | 11/1989 | Edgren et al. | 424/488 |
| 4,983,398 | 1/1991 | Gaylord et al. | 424/465 |
| 4,994,276 | 2/1991 | Baichwal et al. | 424/440 |
| 5,047,248 * | 9/1991 | Calanchi et al. | 424/485 |
| 5,292,534 | 3/1994 | Valentine et al. | 424/451 |
| 5,395,626 | 3/1995 | Kotwal et al. | 424/472 |
| 5,427,799 | 6/1995 | Valentine et al. | 424/45 |
| 5,451,409 | 9/1995 | Rencher et al. | 424/468 |
| 5,662,933 * | 9/1997 | Baichwal et al. | 424/457 |

FOREIGN PATENT DOCUMENTS

| | | |
|---|---|---|
| 0 409 781 | 1/1991 | (EP) . |
| 2 255 344 | 11/1992 | (GB) . |
| 87 00044 | 1/1987 | (WO) . |

OTHER PUBLICATIONS

Alderman, D.A. "A Review of Cellulose Ethers in Hydrophilic Matrices for Oral and Controlled Release Dosage Forms", Int. J. Pharm, Tech & Prod. Mfr. 5(3), 1–9, 1984.

Feely, Liam C.; Davis, Stanley S., The Influence of polymeric excipients on drug release from hydroxpropyl methyl cellulose matrixes, Int. J. Pharm. Date 1988, vol. 44 No. 1–3, pp. 131–139, English CA: 109(10)79581r.

Matsumura, Manabu; Nakagami, Hiroaki; Yamao, Tadanao; Takayama, Kozo; Nagai, Tsuneji, Computer optimiation for the formulation of controlled–release theophylline tablet made of micronized low–substituted bydroxypropyl cellulose and methyl cellulose, Chem. Pharm. Bull. Date: 1994, vol. 42 No. 9, pp. 1902–1908, Enclish CA:122(16)196834e.

* cited by examiner

Primary Examiner—James M. Spear
(74) Attorney, Agent, or Firm—Martin F. Sloan; David Edwards

(57) ABSTRACT

A pharmaceutical composition has a blend of at least first and second components and a medicament in a sufficient amount to be therapeutic where the first component is selected from hydroxypropylcellulose (HPC), ethylcellulose (EC), or derivatives of HPC, EC, and hydroxyethylcellulose (HEC) and the second component is at least one other polymer. When HPC is the first component, hydroxypropylmethylcellulose (HPMC), HEC, or carboxymethylcellulose will not be the second component and when EC is the first component, HPMC will not be the second component. The medicament can be a variety of drugs or nutritional supplements. The pharmaceutical composition releases the medicament for a prolonged or sustained period of time and can be formulated into many dosage forms.

29 Claims, No Drawings

SUSTAINED RELEASE POLYMER BLEND FOR PHARMACEUTICAL APPLICATIONS

This invention relates to a sustained release composition, and, more particularly, to a pharmaceutical composition having a polymer blend that will release a therapeutic agent for a prolonged or sustained period of time.

BACKGROUND OF THE INVENTION

Controlled or sustained release dosage forms are well known in the prior art and make broad use of polymeric compositions to delay or control the release of a medicament or nutritional supplement. Controlled or sustained release dosage forms are desirable because they provide a single dosage application without overdosing the patient and deliver a medicament or nutritional supplement at an appropriate rate to provide the desired activity over periods of time of up to 24 hours. These dosage forms can be formulated into a variety of physical structures or forms, including tablets, lozenges, gelcaps, buccal patches, suspensions, solutions, gels, etc.

Polymer blends in sustained release compositions are known and used in the pharmaceutical industry because of the blend's versatility of being able to create different release profiles. Cellulose ethers are desirable polymers for use in sustained release compositions because they are derived from naturally occurring cellulose, and are free-flowing, readily compressible powders. Unfortunately, not all cellulose ethers provide a desirable release profile for compressed tablets.

Many approaches are disclosed in the prior art for creating blends with unique characteristics. Blending of hydroxypropylmethylcellulose (HPMC) with other polysaccharides is a common blending approach as seen in the prior art. Two examples of this approach are disclosed in U.S. Pat. Nos. 4,389,393 that discloses HPMC and carboxymethylcellulose (CMC) blends and 4,756,911 that discloses HPMC and guar gum blends. Another blending approach is disclosed in U.S. Pat. No. 5,451,409 that blends hydroxypropylcellulose (HPC) with hydroxyethylcellulose (HEC) for use as sustained release pharmaceutical matrix compositions. U.S. Pat. No. 4,704,285 discloses the use of fine particle size HPC alone or blended with HPMC for sustained release applications; U.S. Pat. No. 4,259,314 also discloses the use of the blend of HPMC and HPC with both hygroscopic and non-hygroscopic materials.

Although many different approaches are disclosed in the prior art for creating blends of cellulose ethers, a need still exists in the pharmaceutical industry for having additional cellulose ether polymeric materials that would provide additional flexibility in sufficient release profiles that are stable yet economical for compressed tablets. In addition to providing the desired release rate profile, the polymeric composition should also provide required material properties to the dosage form for safe use and consistent manufacture.

SUMMARY OF THE INVENTION

The present invention is directed to a sustained release pharmaceutical composition comprising a polymer blend formed with a medicament present in a therapeutic amount where the polymer blend contains at least a first component and a second component. The first component is selected from the group consisting of HPC, ethyl cellulose (EC), and derivatives of HPC, EC, and HEC and the second component is at least one other polymer with the proviso that when HPC is the first component, HPMC, HEC or CMC will not be the second component. Another proviso is when EC is the first component, HPMC will not be the second component. A medicament is present in sufficient amount to be therapeutic.

DETAILED DESCRIPTION OF THE INVENTION

It has now been found that the sustained or extended release dosage forms of the present invention make broad use of polymeric compositions to delay or control the release rate of a medicament or nutritional supplement creating a wide range of release profiles for a wide range of medicaments. Through the blending of a wide range of polymers, it is possible to produce equivalent or enhanced tableting performance as well as enhanced sustained or controlled release properties to a wide range of medicaments. The polymeric blends of the present invention, not only improve sustained release characteristics when compared to the individual polymers, but in most cases, in tablet form have shown improved tablet hardness, improved tablet friability and a more manageable and predictable granulation endpoint.

The pharmaceutical compositions of this invention include blends of hydroxypropyl cellulose (HPC), ethyl cellulose (EC) or derivatives of HPC, EC, or HEC with other polysaccharides and their derivatives and synthetic polymers.

This invention provides a controlled or sustained release of a wide range of medicaments or nutritional supplements as well as provides a wide range of material properties to the dosage forms in which they are included. The blend of this invention contains at least two components while three or four or even five components can be used with the number of components being determined primarily by the desired release profile, desired characteristics of the dosage form, and the properties of the drugs.

According to the present invention, the components of the blend are preferably selected so that a dosage form releases the medicament drugs over precise periods of time. The blend in the composition of the present invention should be sufficient to provide the sustained release effect. Typically, the blend should be greater than 5% by weight of the composition of the present invention. Preferably, the blend should be greater than 15%, more preferably greater than 20% with the maximum being dependent upon the drug properties and release profile. A 30% blend is a preferable blend. The upper limit of the amount of the blend in the composition can be 99%, but preferably 95%, and more preferably, 90% dry weight of the composition.

Although a number of polymers may be used in the matrix blend of the present invention, this invention particularly contemplates the use of combinations of either HPC or EC or derivatives of HPC, EC or HEC as the first component with at least one other polymer. A proviso is that HPC cannot be used with HEC, is CMC or HPMC and EC cannot be used with HPMC.

Examples of derivatives of HPC or EC that are useful in the practice of the present invention are anionic modifications, such as carboxymethyl moiety, cationic modifications, such as hydroxypropyltrimethylammonium salts, and nonionic modifications, such as alkyl or arylakyl moiety having 2 to 30 carbons.

Examples of polysaccharides useful in the practice of the present invention are carboxymethylcellulose (CMC), hydroxyethylcellulose (HEC), methylcellulose (MC), ethylhydroxyethylcellulose (EHEC), hydroxyethylmethylcellulose HEMC), hydrophobically modified hydroxyethylcellulose (HMHEC), hydrophobically modified ethylhydroxyethylcellulose (HMEHEC), carboxymethylhydroxyethylcellulose (CMHEC), carboxymethyl hydrophobically modified hydroxyethylcellulose (CMHMHEC), guar and guar derivatives, pectin, carrageenan, xanthan gum, locust bean gum, agar, algin and its derivatives, gellan gum, acacia, starch and modified starches; examples of synthetic polymers are mono- and co-polymers of carboxyvinyl monomers, mono- and co-polymers of acrylates or methacrylates monomers, mono- and co-polymers of oxyethylene, or oxypropylene monomers. All of these second and subsequent components can be used either alone or as mixtures thereof.

According to the present invention, the ratio of the HPC or EC or derivatives of HPC, EC, or HEC to the total amount of the other polymer components in an uncoated dosage form should be in the range of from about 1:99 to 99:1 where the total of these components equals 100 weight percent. A preferred range is 5:95 to 95:1 with a more preferred range being 10:90 to 90:10. Preferred blends are HPC/CMC, HPC/guar, HPC/carboxyvinyl polymer, HPC/carrageenan, and ethyl cellulose/guar. The more preferred blends are those with HPC being the first component.

One or more medicaments may be combined in a single dosage form, depending on the chemical compatibility of the combined active ingredients and the ability to obtain the desired release rate from the dosage form for each active ingredient. The determination of the effective amount of the medicament per dosage unit is easily determined by skilled clinicians.

Representative types of active medicaments include antacids, anti-inflammatory substances, (including but not limited to non-steroidal anti-inflammatory drugs (NSAIDs), vasodilators, coronary vasodilators, cerebral vasodilators, and peripheral vasodilators), anti-infectives, psychotropics, antimanics, stimulants, antihistamines, laxatives, decongestants, vitamins, gastrointestinal sedatives, antidiarrheal preparations, antianginal drugs, antiarrhythmics, antihypertensive drugs, vasoconstrictors and migraine treatments, anticoagulants and anti-thrombotic drugs, analgesics, anti-pyretics, hypnotics, sedatives, antiemetics, anti-nauseants, anticonvulsants, neuromuscular drugs, hyper-and hypoglycemic agents, thyroid and antithyroid preparations, diuretics, antispasmodics, uterine relaxants, mineral and nutritional additives, anti-obesity drugs, anabolic drugs, erythropoietic drugs, antiasthmatics, expectorants, cough suppressants, mucolytics, antiuricemic drugs, and other drugs or substances acting locally in the mouth, such as topical analgesics, local anesthetics, polypeptide drugs, anti-HIV drugs, chemotherapeutic and anti-neoplastic drugs, etc.

Examples of specific active medicaments include aluminum hydroxide, prednisolone, dexamethasone, aspirin, acetaminophen, ibuprofen, isosorbide dinitrate, nicotinic acid, tetracycline, ampicillin, dexbrompheniramine, chlorpheniramine, albuterol, pseudoephedrine, loratadine, theophylline, ascorbic acid, tocopherol, pyridoxine, methoclopramide, magnesium hydroxide, verapamil, procainamide hydrochloride, propranolol, captopril, ergotamine, flurazepam, diazepam, lithium carbonate, insulin, furosemide, hydrochlorothiazide, guaiphenesin, dextromethorphan and benzocaine, although any active medicament which is physically and chemically compatible with the polymer blends and other dosage form ingredients and which demonstrates the desired controlled release characteristics may be used in the present invention.

Formulations containing NSAIDs (including for the purposes of this application acetaminophen) may also contain therapeutic amounts of other pharmaceutical actives conventionally employed with NSAID including but not limited to decongestants or bronchodilators (such as pseudoephedrine, phenylpropanolamine, phenylephrine and pharmaceutically acceptable salts thereof), antitussives (such as caraminophen, dextromethorphan and pharmaceutically acceptable salts thereof, antihistamines (such as chlorpheniramine, brompheniramine, dexchlorpheniramine, dexbrompheniramine, triprolidine, doxylamine, tripelennamine, cyproheptadine, pyrilamine, hydroxyzine, promethazine, azatadine and pharmaceutically acceptable salts thereof), non-sedating antihistamines (such as acrivastine, astemizole, cetirizine, ketotifen, loratidine, temelastine, terfenadine (including the metabolites disclosed in U.S. Pat. Nos. 4,254,129 and 4,285,957 hereby incorporated by reference and pharmaceutically acceptable salts thereof), muscle relaxants (such as glycerylmonoether SMRs, methocarbamol, mephenesin, mephenesin carbamate, cyclobenzaprine, chlorzoxazone, mephenesin acid succinate, chlorphenesin carbamate, or pharmaceutically acceptable salts thereof) and adjuvants (such as diphenhydramine, caffeine, xanthine derivatives (including those disclosed in U.S. Pat. No. 4,558,051, hereby incorporated by reference) and pharmaceutically acceptable salts thereof), nutritional supplements and combinations of any of the aforesaid pharmaceutical. The aforesaid pharmaceuticals may be combined with acetaminophen for the treatment of allergies, coughs, colds, cold-like and/or flu symptoms in mammals including humans. However, these pharmaceuticals may be combined with acetaminophen as sleep aids (such as diphenhydramine), or for other known purposes.

The processing of these sustained release polymer blends may be done by bag mixing two or more components, twin shell V-blending, or co-extrusion. Other standard pharmaceutical processing techniques will also work for these polysaccharide blends. Examples are: high shear mixing, fluid bed processing, spheronization techniques, spray drying, roll compaction and direct compression. Even the simplest processing techniques will impart the required enhanced properties defined here. To insure that the mixture is uniform, the polysaccharides are passed through a screen. The screening step will eliminate any lumps which are present in the materials.

Additionally present with the polymer blends, is at least one other component and active medicament that may be one or more fillers or bulking agents such as dibasic calcium phosphate dihydrate, lactose or starch, with microcrystalline cellulose being the preferred filler. The filler may be present in an amount in the range of from about 0 to about 94 percent of the total weight of the uncoated dosage form, with from about 1 to about 5 weight percent being preferred for very high dose actives and with from about 80 to 85 weight percent being preferred for very low dose actives.

The uncoated dosage form may also contain one or more lubricating agents, e.g., stearic acid, colloidal silicon dioxide, magnesium stearate, calcium stearate, waxes, polyethylene glycol, or magnesium lauryl sulfate, present in an amount of from about 0.25 to about 3 weight percent of the total weight of the uncoated dosage form.

Other ingredients, such as disintegrating agents, coloring agents and flavorings may also be added at the discretion of the manufacturer.

According to the present invention, tablet formulations of the sustained release polymer blends can be used either coated or uncoated. When it is desired to have coated tablets, the coating can be aqueous, solvent, or enteric systems that are well known in the pharmaceutical industry. Coatings can be used for many different reasons depending on the needs or desires of the manufacturer for purposes as widespread as aesthetic to delaying the start of sustained release profile of the tablet to a particular location in the digestive system of a user.

According to this invention, the solid dosage forms can have many forms from a homogeneous or random matrix tablet form to a single homogeneous layer around a core to a bi- or multi-layered dosage form. In the multi-layered controlled release pharmaceutical dosage form of the present invention, a plurality of coating layers including at least two sustained release layers can be used. The number of layers can build up to as many as needed depending on the desired size of the tablet and the release profile. The multi-layered coated particles of the present invention are particularly well suited for very water soluble drugs, since the multicontrol release barrier approach of this invention mitigates the possibility of premature leaching out of very water soluble drugs active in aqueous systems such as the digestive tract.

All work disclosed in this patent was conducted as single layer compressed tablets. The sustained release principles established using this model would also apply to core matrix, bi-layer or multi-layer dosage forms.

TABLET PROCESSING TECHNIQUE

The model drugs used in the examples was Phenylpropanolamine Hydrochloride (PPA) and acetaminophen (APAP). Both drugs are water soluble medicaments chosen to demonstrate the effect of the polymeric blends on the drug release rates.

All of the formulations were made using a low shear mixer (Hobart 12 quart). The materials PPA, Avicel® PH-101 product, and polymers were processed as wet granulations using povidone (PVP) dissolved in water as the granulation aid. Additional water may be required because of the water demand of the particular polymers.

After drying the granulation to an acceptable moisture content, the granulation was milled through a 0.050" screen at high speed using a Fitzpatrick comminutator mill. A portion of the reduced granulation was weighed, blended with Avicel® PH-102 material and magnesium stearate and then compressed into tablets.

The tableting characteristics were profiled using a rotary tablet press (Manesty Beta-Press). The tablets were made on 7/16" standard concave tooling. The tableting results that were studied included tablet friability, compression forces required to make the tablet, and the resultant tablet hardness value.

The model drug release rate for PPA was monitored by performing dissolution testing (USP test method) in deionized water and the results were compared as the time to release 80% of the drug (T80) and the time to release 90% of the drug (T90). The release rate for the APAP model was reported as the time to release 60% of the drug (T60). The USP test method is the dissolution test conducted using a Hewlett Pakard 8452A Diode-Array Spectrophotometer. 500 ml of purified water is used as the medium. The test is conducted at 37° C., with baskets rotating at 100 RPM. The test is run for 16 hours. The dissolution test results for the drug release are reported as T80 and T90.

All of the polymeric blends tested in the drug tablet formulations contained polymer blends which were incorporated into the tablet at a 30% weight, based on the total tablet composition. This 30% level was kept constant throughout all of the comparisons.

The use of the above-mentioned combinations produced the improved tableting characteristics as well as the necessary sustained release or controlled release properties for the model medicament.

The working formulation for the Examples contained the ingredients as shown in the formulation found in Table 1. The numbers are reported as percent weight basis of the total blend unless otherwise stated.

TABLE 1

|  | %/Tablet |
| --- | --- |
| Wet Granulation Step | |
| SR Blend (Component 1 & 2) | 30.0% |
| Phenylpropanolamine HCl | 15.0% |
| Avicel ® PH-101 | 32.4% |
| Povidone(Polyvinylpyrrolidone) | 2.4% |
| Water | As Needed |
| Dried Granulation/Final Blend | |
| Dried/Reduced Granulation | 79.8% |
| Avicel ® PH-102 | 19.2% |
| Magnesium stearate | 0.1% |

Avicel ® PH-101 is a trademark used to cover a microcrystalline cellulose product marketed by FMC Corporation; PH-101 is a grade designation denoting that the average particle size is 50 μ and PH-102 has an average particle size of 100 μ.

The formulation shows the amounts of the raw materials used in these test experiments. The amount of water used to form the granulation varied because of the water demand differences caused by the polysaccharide blends.

EXAMPLE 1

This example describes ten different formulations of a solid oral dosage form containing an active medicament, PPA, and a variety of HPC (Component 1) and CMC or guar (Component 2) polysaccharide concentrations. TABLE 2 shows the formulations which contain polysaccharide blends of KLUCEL® HXF polymer and either CMC or guar. TABLE 3 shows the formulations which contain polysaccharide blends of KLUCEL® HF polymer and either Aqualon® CMC 7L2P, USP or Supercol® U guar gum, USP.

TABLE 2

|  | A | B | C | D | E | F |
| --- | --- | --- | --- | --- | --- | --- |
| Wet Granulated Materials | | | | | | |
| KLUCEL ® HXF, NF | 37.5 mg | 75 mg | 112.5 mg | 37.5 mg | 75 mg | 112.5 mg |
| Aqualon ® CMC 7L2P, USP | 112.5 | 75 | 37.5 | | | |
| Guar (SUPERCOL ® U, USP) | | | | 112.5 | 75 | 37.5 |

TABLE 2-continued

|  | A | B | C | D | E | F |
|---|---|---|---|---|---|---|
| PPA, USP | 75 | 75 | 75 | 75 | 75 | 75 |
| Avicel ® PH-101, NF | 162 | 162 | 162 | 162 | 162 | 162 |
| Final Blend Materials | | | | | | |
| Reduced Granulation | 399 mg | 399 mg | 399 mg | 399 mg | 399 mg | 399 mg |
| Avicel ® PH-102, NF | 96 | 96 | 96 | 96 | 96 | 96 |
| Magnesium Stearate, NF | 5 | 5 | 5 | 5 | 5 | 5 |
| Total Table Weight | 500 mg | 500 mg | 500 mg | 500 mg | 500 mg | 500 mg |

KLUCEL HXF, Aqualon, and SUPERCOL U are trademarks that denote products marketed by Aqualon Company of Hercules Incorporated. KLUCEL HXF trademark is used to market a finely ground hydroxypropylcellulose product. SUPERCOL U trademark is used to market a highly refined pure edible guar gum product. Avicel PH-101 is a trademark used to cover a microcrystalline cellulose product marketed by FMC Corporation. USP means United States Pharmacopeia. NF means National Formulary.

TABLE 3

|  | G | H | I | J |
|---|---|---|---|---|
| Wet Granulated Materials | | | | |
| Hydroxypropylcellulose, NF (Finely Ground, KLUCEL ® HF) | 75 mg | 112.5 mg | 75 mg | 112.5 mg |
| Aqualon ® CMC 7L2P | 75 | 37.5 | | |
| Guar (SUPERCOL ® U) | | | 75 | 37.5 |
| PPA, USP | 75 | 75 | 75 | 75 |
| Avicel ® PH-101, NF | 162 | 162 | 162 | 162 |
| Providone (PVP), NF | 12 | 12 | 12 | 12 |
| Final Blend Materials | | | | |
| Reduced Granulation | 399 mg | 399 mg | 399 mg | 399 mg |
| Avicel ® PH-102, NF | 96 | 96 | 96 | 96 |
| Magnesium Stearate, NF | 5 | 5 | 5 | 5 |
| Total Table Weight | 500 mg | 500 mg | 500 mg | 500 mg |

KLUCEL HF is a trademark that denotes a granular solid HPC product that has particle sizes where 85% passes through 30 mesh screen and 99% passes through 20 mesh screen of a US standard sieve and is marketed by Aqualon Company of Hercules incorporated.

TABLE 4 provides a comparison of the blends made using KLUCEL® HXF polymer and either Aqualon® CMC 7L2P or SUPERCOL® U guar in the PPA formulation with respect to tablet performance and dissolution T80 and T90 results. The tablet hardness and friability results are for tablets made using 15 kN compression force. Also, included in this table for comparative purposes are the results for 100% CMC 7L2P and SUPERCOL® U guar.

TABLE 4

|  | Hardness | Friability | Score Strength* | | T80 | T90 |
|---|---|---|---|---|---|---|
|  | (Kp) | (% loss) | 15 kN | 25 kN | (min) | (min) |
| KLUCEL ® HXF/ CMC 7L2P | | | | | | |
| Ratio 25/75 | 8.5 | 0.040 | 211 | 673 | 121 | 148 |
| Ratio 49/51 | 11.4 | 0.040 | 734 | 980 | 318 | 428 |
| Ratio 75/25 | 14.5 | 0.020 | 728 | 922 | 392 | 554 |
| 100% CMC 7L2P | 4.8 | 0.481 | 10 | 233 | 88 | 104 |
| KLUCEL ® HXF/SUPER- COL ® U | | | | | | |
| Ratio 25/75 | 12.5 | 0.020 | 35 | 900 | 267 | 364 |
| Ratio 49/51 | 14.6 | 0.020 | 734 | 980 | 318 | 428 |
| Ratio 75/25 | 14.9 | 0.020 | 750 | 902 | 323 | 436 |
| 100% SUPERCOL ® U | 9.1 | 0.080 | 114 | 781 | 235 | 327 |

*Score Strength value is defined as the value derived by dividing the tablet hardness value by the tablet friability value.

As can be seen from TABLE 4, the polysaccharide blends made using KLUCEL® HXF polymer and CMC 7L2P provide improved tablet performance and prolonged T80 and T90 dissolution results at all ratios compared to 100% CMC 7L2P. Better performance was seen at the ratios of 49/51 and 75/25 than when the ratio was 25/75.

Also, seen in the blends of KLUCEL® HXF material and SUPERCOL® U guar was a similar trend. At the blend ratios of 49/51 and 75/25 these polysaccharide combinations showed marked improvement of tablet physical properties as well as prolonged T80 and T90 dissolution times.

The improved tableting performance and prolonged dissolution release rates were unique properties that were found with these polymer blends.

TABLE 5 provides a comparison of the blends made using KLUCEL® HF polymer and either CMC 7L2P or SUPERCOL® U guar in the PPA model formulation. The tablet performance and dissolution T80 and T90 results are shown. The tablet hardness and friability results are for tablets compressed using 15 kN of force. The results of 100% CMC 7L2P and SUPERCOL® U product have been included for comparison.

TABLE 5

|  | Hardness | Friability | Score Strength | | T80 | T90 |
|---|---|---|---|---|---|---|
|  | (Kp) | (% loss) | 15 kN | 25 kN | (min) | (min) |
| KLUCEL ® HF/ CMC 7L2P | | | | | | |
| Ratio 50/50 | 8.0 | 0.060 | 134 | 573 | 182 | 220 |
| Ratio 75/25 | 8.6 | 0.060 | 144 | 548 | 339 | 513 |
| 100% | 4.8 | 0.481 | 10 | 233 | 88 | 104 |

TABLE 5-continued

|  | Hardness | Friability | Score Strength | | T80 | T90 |
|---|---|---|---|---|---|---|
|  | (Kp) | (% loss) | 15 kN | 25 kN | (min) | (min) |
| CMC 7L2P KLUCEL® HF/SUPER-COL® U | | | | | | |
| Ratio 50/50 | 11.5 | 0.020 | 572 | 730 | 239 | 342 |
| Ratio 75/25 | 11.4 | 0.020 | 572 | 731 | 240 | 349 |
| 100% SUPER-COL® U | 9.1 | 0.080 | 114 | 781 | 235 | 327 |

The results reported in TABLE 5 indicate that KLUCEL® HF polymer at blend ratios of 50/50 or 75/25 in combination with either CMC 7L2P or SUPERCOL® U material have enhanced tableting performance and prolonged T80 and T90 dissolution test results when compared to the unblended CMC 7L2P or SUPERCOL® U material.

EXAMPLE 2

This Example illustrates blends of HPC and carrageenan for solid dosage form (tablets). The standard tablet processing technique was used. Table 6 shows the components of the composition and Table 7 shows the properties.

TABLE 6

|  | K | L | M | N |
|---|---|---|---|---|
| Wet Granulated Materials | | | | |
| KLUCEL® HF | 150 mg | 75 mg | 112.5 mg |  |
| Carrageenan (GENUVISCO® type X-0908) |  | 75 | 37.5 | 150 mg |
| PPA | 75 | 75 | 75 | 75 |
| Avicel® PH-101, NF | 162 | 162 | 162 | 162 |
| PVP, NF | 12 | 12 | 12 | 12 |
| Final Blend Materials | | | | |
| Reduced Granulation | 399 mg | 399 mg | 399 mg | 399 mg |
| Avicel® PH-102, NF | 96 | 96 | 96 | 96 |
| Magnesium Stearate, NF | 5 | 5 | 5 | 5 |
| Total Tablet Weight | 500 mg | 500 mg | 500 mg | 500 mg |

TABLE 7

|  | Hardness | Friability | Score Strength | | T80 | T90 |
|---|---|---|---|---|---|---|
|  | (Kp) | (% Loss) | 15 kN | 25 kN | (Min) | (Min) |
| HF/GENU-VISCO® (type X-0908) | | | | | | |
| Ratio 50/50 | 13.2 | .060 | 221 | 914 | 295 | 355 |
| Ratio 75/25 | 13.0 | .040 | 324 | 818 | 413 | 5.59 |
| 100% KLUCEL® HF | 7.9 | .060 | 129 | 460 | 244 | 332 |
| 100% GENU-VISCO® type X-0908 | 13.0 | .020 | 648 | 897 | 114 | 134 |

Once again the data shows that the polysaccharide blends of KLUCEL® HF material and GENUVISCO® type X-0908 carrageenan out performed the individual components. The tablet hardness values were very similar for the blend ratios of 50/50 and 75/25. At the 75/25 ratio the sustained release performance was better than the ratio of 50/50. The preferred ratio for these polymer blends is 75/25.

EXAMPLE 3

This Example illustrates a modified tableting process based on the standard process used in the above Examples. The modification is that the granulations were made using KLUCEL® EXF HPC as the binder. Avicel® PH-102 material was added to the dried, reduced granulation and blended for 3 minutes in a 4-quart V-blender. The sustained release polymer blend was then added and blended for 5 minutes. Finally, the screened (through 20 mesh) magnesium stearate was added and blended for 3 minutes. Tablets were compressed on 7/16" SC tablet tooling. The composition components are shown in Table 8 and the properties of the tablets are shown in Table 9 below.

TABLE 8

| Wet Granulated Materials | |
|---|---|
| KLUCEL® EXF | 20 mg |
| PPA | 75 mg |
| Avicel® PH-101, NF | 76 mg |
| PVP, NF | 12 mg |

| Final Blend Materials | | | |
|---|---|---|---|
|  | O | P | Q |
| Reduced Granulation (A) | 183 mg | 183 mg | 183 mg |
| KLUCEL® HF | 150 | 112.5 | 112.5 |
| SUPERCOL® U |  | 37.5 |  |
| Carbopol® 971P |  |  | 37.5 |
| Avicel® PH-102, NF | 162 | 162 | 162 |
| Magnesium Stearate, NF | 5 | 5 | 5 |
| Total Tablet Weight | 500 mg | 500 mg | 500 mg |

KLUCEL EXF is a registered trademark of the Aqualon Co. under which finely ground HPC is marketed.
Carbopol 971P is a registered trademark of the B F Goodrich Co. under which Acrylic polymer, carboxy polymethylene, or carbomers are marketed.

TABLE 9

|  | Hardness | Friability | Score Strength | | T80 | T90 |
|---|---|---|---|---|---|---|
|  | (Kp) | (% Loss) | 15 kN | 25 kN | (Min) | (Min) |
| 100% KLUCEL® HF | 14.5 | 0.140% | 103 | 297 | 230 | 335 |
| KLUCEL® HF/SUPER-COL® U ratio 75/25 | 13.3 | 0.20% | 66 | 124 | 253 | 358 |
| KLUCEL® HF/Carbopol 971P ratio 75/25 | 17.4 | 0.20% | 873 | 1120 | 405 | 572 |

The data for these formulations, as reported in TABLE 9, shows that the sustained release polymer blend containing KLUCEL® HF polymer and Carbopol 971P polymer at the ratio of 75/25 worked well with respect to the tableting performance as well as it sustained release properties. The blend composed of KLUCEL® HF/SUPERCOL® U materials also showed improved sustained release properties, when compared to KLUCEL® HF polymer alone.

This Example showed that KLUCEL® HF/Carbopol® 971P blend at the 75/25 ratio is the preferred composition.

EXAMPLE 4

This Example illustrates blends of EC and guar for tablets using the standard tablet processing technique noted above except that in experiment U the SR polymer blend was added in as final blend materials. Table 11 shows the properties of the tablets of these experiments.

TABLE 10

|  | R | S | T | U |
|---|---|---|---|---|
| Wet Granulated Materials | | | | |
| Ethylcellulose, N-7, NF | 150 mg | 75 mg | 37.5 mg | |
| Guar (SUPERCOL ® U) | | 75 | 112.5 | |
| KLUCEL ® EXF | | | | 20 |
| PPA | 75 | 75 | 75 | 75 |
| Avicel ® PH-102, NF | 162 | 162 | 162 | 76 |
| PVP, NF | 12 | 12 | 12 | 12 |
| Final Blend Materials | | | | |
| Reduced Granulation | 399 mg | 399 mg | 399 mg | 183 mg |
| Guar (SUPERCOL ® U) | | | | 112.5 |
| EC N-7 | | | | 37.5 |
| Avicel ® PH-102, NF | 96 | 96 | 96 | 162 |
| Magnesium Stearate, NF | 5 | 5 | 5 | 5 |
| Total Tablet Weight | 500 mg | 500 mg | 500 mg | 500 mg |

TABLE 11

|  | Hardness | Friability | Score Strength | | T80 | T90 |
|---|---|---|---|---|---|---|
|  | (Kp) | (% Loss) | 15 kN | 25 kN | (Min) | (Min) |
| EC/SUPERCOL ® U | | | | | | |
| Ratio 50/50 | 18.8 | 0.140% | 471 | 1194 | 165 | 236 |
| Ratio 75/25 | 23.5 | 0.020% | 1174 | 1445 | 60 | 87 |
| 100% EC N-7, NF | 22.0 | 0.020% | 1110 | 1346 | 100 | 114 |
| EC/SUPERCOL ® U* Ratio 25/75 | 10.5 | 0.340% | 32 | 65 | 207 | 272 |

As the data shows in Table 11, there are prolonged T80 and T90 dissolution test results for the ratio of 50/50 blends when compared to the 100% EC N-7 and blend ratio 75/25 test results. The tableting results show that this blend ratio (50/50) has good performance. It appears that the best ratio of EC N-7/SUPERCOL® U is 50/50 when the sustained release polymers are included in the granulated materials.

In Experiment U, the EC/SUPERCOL® U 25/75 blend ratio when added in the final blend materials gave good T80 and T90 test results.

EXAMPLE 5

Acetaminophen was used as the medicament in this Example to show its efficacy in polymer blends for sustained release applications. The formulation contained 50% acetaminophen (APAP). The manufacturing steps were as follows:

A polymer blend of KLUCEL® HF/SUPERCOL® U polymers and APAP were screened through a 20 mesh screen. These materials were dry blended in a 12-quart Hobart mixer for 2 minutes. PVP was dissolved in 200 g of purified water. The binder solution and any additional water required was added and the materials were granulated to a suitable endpoint. The granulation was tray dried until the moisture content was less than 2%.

The dried granulation was milled using a Fitzmill using knives forward, 0.065" screen and medium speed. The reduced granulation was placed in a V-blender, magnesium stearate was added and then blended for 2 minutes. The final blend materials were then compressed on a Beta-press fitted with ½ inch standard concave tooling.

Table 12 shows the formulations. Table 13 shows the results found from tableting and testing these batches.

TABLE 12

|  | Aa | Bb | Cc |
|---|---|---|---|
| Wet Granulation Materials | | | |
| Acetaminophen | 325 mg | 325 mg | 325 mg |
| KLUCEL ® HF | 195 | 97.5 | 146.25 |
| SUPERCOL ® U | | 97.5 | 48.75 |
| Avicel ® PH-101, NF | 108 | 108 | 108 |
| PVP, NF | 15.6 | 15.6 | 15.6 |
| Final Blend Materials | | | |
| Magnesium Stearate, NF | 6.5 | 6.5 | 6.5 |
| Total Table Weight | 650 mg | 650 mg | 650 mg |

TABLE 13

|  | Hardness | Friability | Score Strength | | T60 |
|---|---|---|---|---|---|
|  | (Kp) | % Loss | 15 kN | 25 kN | (Min) |
| 100% KLUCEL ® HF | 7.2 | 1.349 | 5 | 9 | 41.2 |
| KLUCEL ® HF/SUPERCOL ® U | | | | | |
| ratio 50/50 | 5.5 | 9.373 | 1 | 28 | 619.7 |
| ratio 75/25 | 6.1 | 1.995 | 3 | | 20 |

The results set forth in Table 13 show the strong sustained release characteristics of the KLUCEL® HF/SUPERCOL® U 50/50 blend using the acetaminophen drug. The acetaminophen model that inherently has poor compression characteristics attributed to the high friability and low hardness values of this study.

Another advantage of these sustained release polymer blend systems is that they have longer granulation mix times when compared to KLUCEL® HXF polymer. This is a valuable characteristic. Longer granulation mix times permits the formulator to recognize an endpoint more easily. Granulations that reach a quick endpoint can be easily overworked and produce unacceptable products.

TABLE 14

| Polymer or Polymer Blends | Granulation Endpoint Time |
|---|---|
| 100% KLUCEL ® HXF | 1 minute, 42 seconds |
| 100% CMC 7L2P | 12 minutes |
| KLUCEL ® HXF/CMC 7L2P, ratio 25/75 | 7 minutes |
| KLUCEL ® HXF/CMC 7L2P, ratio 49/51 | 4 minutes |
| KLUCEL ® HXF/CMC 7L2P, ratio 75/25 | 4 minutes |
| 100% SUPERCOL ® U | 7 minutes, 30 seconds |
| KLUCEL ® HXF/SUPERCOL ® U, ratio 25/75 | 5 minutes, 30 seconds |
| KLUCEL ® HXF/SUPERCOL ® U, ratio 49/51 | 3 minutes, 30 seconds |
| KLUCEL ® HXF/SUPERCOL ® U, ratio 75/25 | 2 minutes |
| 100% KLUCEL ® HF | 6 minutes, 30 seconds* |
| KLUCEL ® HF/CMC 7L2P, ratio 50/50 | 9 minutes |
| KLUCEL ® HF/CMC 7L2P, ratio 75/25 | 9 minutes |
| KLUCEL ® HF/SUPERCOL ® U, ratio 50/50 | 10 minutes, 30 seconds |
| KLUCEL ® HF/SUPERCOL ® U, ratio 75/25 | 9 minutes, 30 seconds |
| KLUCEL ® HF/GENUVISCO type X-0908, ratio 50/50 | 5 minutes |

TABLE 14-continued

| Polymer or Polymer Blends | Granulation Endpoint Time |
| --- | --- |
| KLUCEL ® HF/GENUVISCO type X-0908, ratio 75/25 | 6 minutes |
| 100% ETHYLCELLULOSE (EC), N7 | 5 minutes |
| ETHYLCELLULOSE, N7/SUPERCOL ® U ratio 50/50 | 7 minutes, 30 seconds |
| ETHYLCELLULOSE, N7/SUPERCOL ® U ratio 75/25 | 7 minutes |

*This formulation had slow liquid addition in an attempt to slow the time to the granulation endpoint.

TABLE 14 shows that all granulation endpoints seen in the PPA model formulation were greatly extended beyond the granulation endpoint that was achieved when KLUCEL® HXF polymer was used alone. The formation of a slow, less dramatic endpoint makes these polymer blend systems valuable to the formulator and process operator.

The foregoing is exemplary and illustrative of compositions and products relative to the present invention, but is not to be considered as a limitation of the present invention. Many other active medicaments of various types can be employed in the new long-lasting carrier matrix of the present invention so long as the medicaments are absorbable into the blood stream or tissue in the general intestinal tract and other bodily surfaces and mucosal areas.

What is claimed is:

1. A pharmaceutical composition comprising a blend of at least first and second components, where the first component is selected from the group consisting of derivatives of HPC, EC, and hydroxyethylcellulose (HEC) where the derivative is an anionic, cationic, or nonionic modification and the second component is at least one other polymer selected from the group consisting of carboxymethylcellulose (CMC), hydroxyethylcellulose (HEC), methylcellulose (MC), ethylhydroxyethylcellulose (EHEC), hydroxyethylmethylcellulose (HEMC), hydrophobically modified hydroxyethylcellulose (HMHEC), hydrophobically modified ethylhydroxyethylcellulose (HMEHEC), carboxymethylhydroxyethylcellulose (CMHEC), carboxymethyl hydrophobically modified hydroxyethylcellulose (CMHMHEC), guar, pectin, carrageenan, xanthan gum, locust bean gum, agar, algin, gellan gum, acacia, starch and modified starches, mono- and co-polymers of carboxyvinyl monomers, mono- and co-polymers of acrylate or methacrylate monomers, mono- and co-polymers of oxyethylene and oxypropylene and mixtures thereof and a medicament in a sufficient amount to be therapeutic.

2. The composition of claim 1 wherein at least one member selected from the group consisting of filler, bulking agent, disintegrating agents, coloring agents, and flavorings is present.

3. The composition of claim 1, wherein the ratio of the first component to the sum of the second and any other components is 1:99 to 99:1.

4. The composition to claim 1 wherein the medicaments are selected from the group consisting of antacids, anti-inflammatory substances, anti-infectives, psychotropics, antimanics, stimulants, antihistamines, laxatives, decongestants, nutritional supplements, gastrointestinal sedatives, antidiarrheal preparations, antianginal drugs, antiarrhythmics, antihypertensive drugs, vasoconstrictors and migraine treatments, anticoagulants and anti-thrombotic drugs, analgesics, anti-pyretics, hypnotics, sedatives, antiemetics, anti-nauseants, anticonvulsants, neuromuscular drugs, hyper-and hypoglycemic agents, thyroid and antithyroid preparations, diuretics, antispasmodics, uterine relaxants, mineral and nutritional additives, anti-obesity drugs, anabolic drugs, erythropoietic drugs, antiasthmatics, expectorants, cough suppressants, mucolytics, antiuricemic drugs, topical analgesics, local anesthetics, poly peptide drugs, anti-HIV drugs, chemotherapeutic and anti-neoplastic drugs.

5. The composition of claim 4 wherein the medicaments are selected from the group consisting of phenylpropanolamine hydrochloride, aluminum hydroxide, prednisolone, dexamethasone, aspirin, acetaminophen, ibuprofen, isosorbide dinitrate, nicotinic acid, tetracycline, ampicillin, dexbrompheniramine, chlorpheniramine, albuterol, pseudoephedrine, loratadine, theophylline, ascorbic acid, tocopherol, pyridoxine, methoclopramide, magnesium hydroxide, verapamil, procainamide hydrochloride, propranolol, captopril, ergotamine, flurazepam, diazepam, lithium carbonate, insulin, furosemide, hydrochlorothiazide, guaiphenesin, dextromethorphan, and benzocaine.

6. The composition of claim 4 wherein the anti-inflammatory substances are selected from the group consisting of non-steroidal anti-inflammatory drugs (NSAIDs), vasodilators, coronary vasodilators, cerebral vasodilators, and peripheral vasodilators.

7. The composition of claim 1 wherein the composition is in the dosage form selected from a group consisting of tablets, lozenges, gelcaps, buccal patches, suspensions, solutions, and gels.

8. The composition of claim 7 wherein the dosage form is tablets.

9. The composition of claim 8 wherein the tablet is coated.

10. The composition of claim 5 wherein the medicament is acetaminophen.

11. The composition of claim 1 wherein at least one lubricating agent is present.

12. The composition of claim 11, wherein the lubricating agent is selected from the group consisting of stearic acid, colloidal silicon dioxide, magnesium stearate, calcium stearate, waxes, polyethylene glycol, and magnesium lauryl sulfate.

13. The composition of claim 11 wherein the lubricating agent is present in the amount of from about 0.25 to 3.0 weight percent of the total weight of the uncoated dosage form.

14. The composition of claim 1 wherein the first component is a derivative of HPC.

15. The composition of claim 1 wherein the second component is selected from the group consisting of guar, carboxymethylcellulose, carrageenan, carboxyvinyl polymer, hydroxypropylcellulose, hydroxyethylcellulose, ethylcellulose, and hydroxypropylmethylcellulose.

16. The composition of claim 1 wherein the first component is a derivative of EC.

17. The composition of claim 16 wherein the second component is selected from the group consisting of guar, carboxymethylcellulose, carrageenan, carboxyvinyl polymer, hydroxypropylcellulose, hydroxyethylcellulose, ethylcellulose, and hydroxypropylmethylcellulose.

18. The composition of claim 1 wherein the first component is a derivative of HEC.

19. The composition of claim 18 wherein the second component is selected from the group consisting of guar, carboxymethylcellulose, carrageenan, carboxyvinyl polymer, hydroxypropylcellulose, hydroxyethylcellulose, ethylcellulose, and hydroxypropylmethylcellulose.

20. The composition of claim 1 wherein a third component is present.

21. The composition of claim 20 wherein third component is carboxyvinyl polymer.

22. The composition of claim 1 wherein the blend has a lower limit of 5% by weight of the composition.

23. The composition of claim 1 wherein the blend has a lower limit of 15% by weight of the composition.

24. The composition of claim 1 wherein the blend has a lower limit of 20% by weight of the composition.

25. The composition of claim 1 wherein the blend is 30% by weight of the composition.

26. The composition of claim 1 wherein the blend has a upper limit of 99% by weight of the composition.

27. The composition of claim 1 wherein the blend has an upper limit of 95% by weight of the composition.

28. The composition of claim 1 wherein the blend has an upper limit of 90% by weight of the composition.

29. The composition of claim 5 wherein the medicament is phenylpropanolamine hydrochloride.

* * * * *